United States Patent [19]

Helfer

[11] 4,325,387
[45] Apr. 20, 1982

[54] SEALING APPARATUS FOR INTRAUTERINE PRESSURE CATHETER AND THE LIKE

[75] Inventor: Joel N. Helfer, Cheshire, Conn.

[73] Assignee: American Home Products Corporation, New York, N.Y.

[21] Appl. No.: 103,876

[22] Filed: Dec. 17, 1979

[51] Int. Cl.³ .......................... A61B 5/00; A61B 17/42
[52] U.S. Cl. .................................... 128/748; 128/772; 128/778; 128/349 R; 285/177; 285/235
[58] Field of Search ............ 128/748, 772, 657, 214.4, 128/757, 758, 759, 778, 214.2, 349 R, 247, 334 C, 350 R; 285/235, 236, 260, 177

[56] References Cited

U.S. PATENT DOCUMENTS

| | | | |
|---|---|---|---|
| 144,163 | 10/1873 | Taylor | 285/260 |
| 812,020 | 2/1906 | Crippen | 128/350 R |
| 1,598,283 | 8/1926 | Kinney | 128/350 R |
| 2,740,404 | 4/1956 | Kohl | 128/214.4 X |
| 2,920,908 | 1/1960 | Mitchell | 285/236 |
| 3,513,830 | 5/1970 | Kalayjian | 128/759 |
| 3,559,643 | 2/1971 | Pannier et al. | 128/214.4 |
| 3,777,743 | 12/1973 | Binard et al. | 128/278 X |
| 4,136,681 | 1/1979 | Hon | 128/748 |
| 4,252,131 | 2/1981 | Hon et al. | 128/748 |

Primary Examiner—Robert W. Michell
Assistant Examiner—John C. Hanley
Attorney, Agent, or Firm—Eugene L. Flanagan, III

[57] ABSTRACT

An apparatus used for measuring the pressure within a body cavity and methods of manufacturing and using same. An elongated catheter has its perforated body end disposed in a guide tube used for introducing the catheter. Both the catheter and guide tube are prefilled with sterile liquid and sealed against loss thereof and disposition of the guide tube and catheter. The gauge end of the guide tube is releasably sealed and secured by a tubular member fitted frictionally over the gauge end of the guide tube and catheter.

9 Claims, 6 Drawing Figures

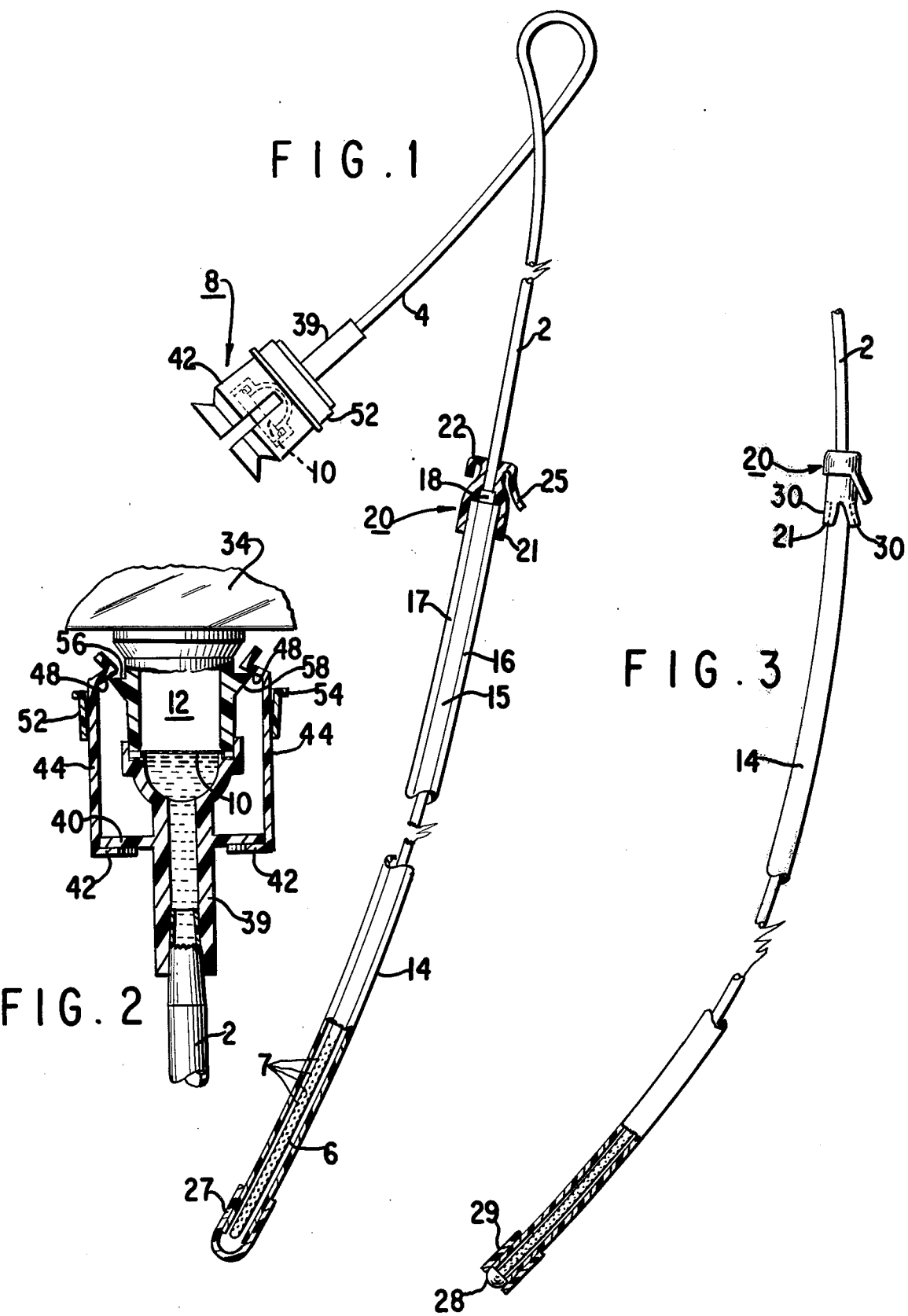

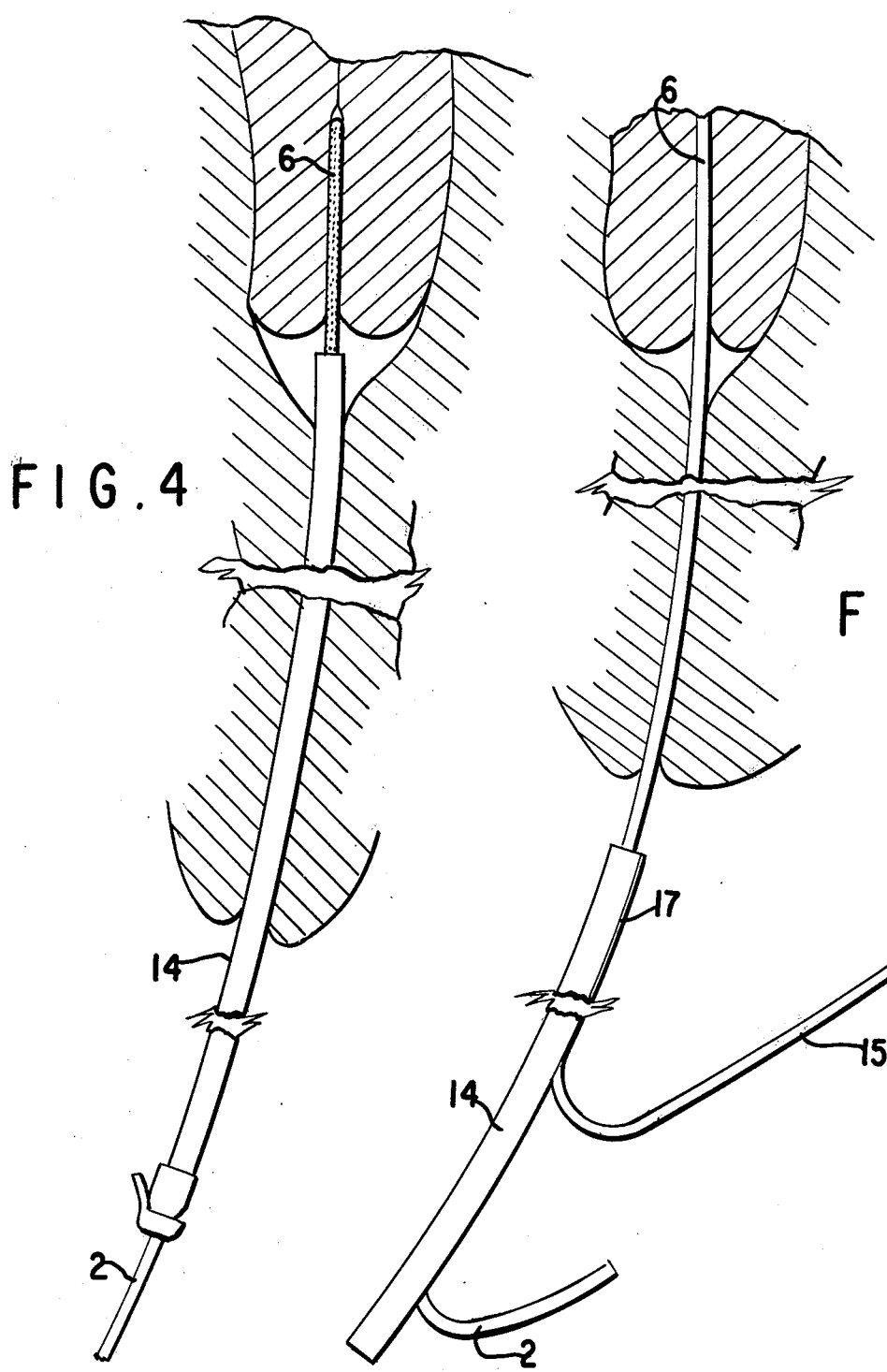

SEALING APPARATUS FOR INTRAUTERINE PRESSURE CATHETER AND THE LIKE

BACKGROUND

This invention concerns the measurement of pressure within a body cavity. More specifically, this invention relates to novel sealing devices for use with a fluid filled pressure catheter enclosed within a guide tube for introduction into a body cavity.

Fetal monitoring is a standard procedure for monitoring the condition of a fetus during childbirth. In most cases, fetal heart rate and intrauterine pressure are measured and separately plotted on a strip-chart recorder. By examining these curves, the onset of certain distress conditions can be detected so that appropriate remedial action can be taken earlier than would otherwise be possible.

To measure intrauterine pressure a catheter may be inserted into the uterus and filled with liquid so that the force of the intrauterine contractions can be transmitted through the uterine fluids and the liquid in the catheter to a pressure-measuring device such as a strain gauge or the like.

An intrauterine pressure catheter which may be used effectively to make measurements of uterine contractions is disclosed in U.S. Pat. No. 4,136,681 in the name of Edward H. Hon which is assigned to the assignee of the present application. U.S. Pat. No. 4,136,681 discloses an elongated catheter filled with liquid and having a perforated body end adapted to be inserted through the vagina and cervix of a woman in labor to measure intrauterine pressure. The end of the catheter opposite the body end, the gauge end, is adapted to be connected to a transducer. A curved guide tube fitted over the body end of the catheter is adapted to introduce the catheter through the woman's vagina.

At the time of manufacture, the guide tube is filled with a sterile liquid in order to minimize the likelihood of introducing air into the catheter tube during transit and use. The entire device is sealed by a suitable polymeric film which is water tight. The film must be punctured to permit entry of the catheter into the uterus and must be torn along its length to permit removal of the guide tube from around the catheter. The principal drawback of the device is that it is relatively difficult and expensive to manufacture.

U.S. Pat. No. 4,252,131, in the names of Edward H. Hon and Carmelo Dali, assigned to the assignee of the present application, discloses an improved catheter for measuring intrauterine pressure wherein the guide tube is scored along its length in two score lines and a tab is affixed to the portion of the guide tube defined by the score lines so that at the time of use, the tab may be separated from the catheter to hold the portion of the guide tube so defined away from the tube. This defines a longitudinal slot through which the catheter can pass so that the guide tube may be removed therefrom.

An outer tubular sheath or envelope receives the catheter within the guide tube and the entire assembly is filled with liquid. The envelope is sealed at its maternal end by a plug, while the gauge end of the envelope is sealed above the gauge end of the guide tube with a hollow elastomeric plug disposed about the circumference of the catheter and compressably fitted into the gauge end of the envelope. A cylindrical friction collar is slid over the envelope to compress the plug to form a liquid tight seal and to prevent relative axial movement of the catheter, guide tube and envelope.

When it is desired to apply the catheter to a patient, the envelope must first be removed from the catheter-guide tube assembly. The friction collar is displaced by turning it and sliding it axially toward the maternal end of the envelope, thereby relieving the pressure on the plug. The latter can then be removed from the envelope and from the catheter via a slit in its wall. The catheter-guide tube assembly is then removed from the envelope for insertion through the vaginal canal of the patient.

In the prior art it was thought necessary to maintain the maternal end of the guide tube sealed until after it had been inserted through the vaginal canal to a point adjacent the cervix. Accordingly, the maternal end of the guide tube was scored at two intersecting lines so that the catheter could be pushed therethrough and beyond into the uterus through the cervix in order to insure that fluid would remain in the catheter.

SUMMARY OF THE INVENTION

In accordance with one embodiment of the present invention, an apparatus for use in measuring the pressure within a body cavity is provided having a catheter filled with liquid and positioned at its body end within a guide tube adapted to define a path within the body through which the catheter is to be advanced. A connector for releasably securing the catheter in a fixed relation to the guide tube comprises a member fitted frictionally over the gauge end of the guide tube and catheter to form a fluid tight seal therebetween. Where a scored guide tube is employed, the connector means serves further to restrain premature separation of the scored portion of the guide tube which would render the apparatus unusable.

In a preferred embodiment of the present invention, the member of the connector means comprises a stretchable, tubular member having an inner diameter intermediate to the outside diameters of the guide tube and the catheter. The tubular member is fitted at one end around the gauge end of the guide tube to form a frictional, fluid tight seal therewith. The other end of the tubular member is rolled axially over a portion thereof thus to force this portion frictionally against the catheter forming a fluid tight seal therewith. The frictional seal between the catheter and the guide tube is easily broken by unrolling the tubular member which then permits removal of the guide tube from the patient by sliding it up the catheter from which it may then be removed by removing the scored portion of the guide tube and sliding the catheter through the longitudinal slot thus formed.

In another embodiment of the invention, a releasable seal is provided to prevent fluid leakage from the guide tube and catheter at the body end thereof. Accordingly, there is no need for an outer envelope of the type shown in U.S. Pat. No. 4,252,131 described hereinabove to prevent loss of fluid from the catheter and guide tube so that the apparatus is relatively easy to use and inexpensive to manufacture.

In accordance with a further aspect of the present invention, an apparatus for use in measuring the pressure within a body cavity is assembled in accordance with the following method. A catheter subassembly is provided having a sealed gauge end and a perforated body end. A guide tube is positioned over the body end of the catheter subassembly. The guide tube has a stretchable tubular member fitted around its gauge end.

The tubular member has an inside diameter larger than the outside diameter of the catheter such that one end of the tubular member protrudes over the catheter. One end of the tubular member is rolled axially over a portion of itself to force this portion frictionally against the catheter forming a fluid tight seal therewith. The catheter and guide tube are filled with a fluid through an opening defined by the body end of the guide tube. The body end of the guide tube is then sealed such that such that loss of fluid from the catheter and guide tube prior to use is substantially prevented.

In a particularly advantageous method of assembling the apparatus, the sealed catheter and guide tube is placed in a package having a low fluid vapor transmissivity. The package is provide with a reservoir of the fluid filling the catheter and guide tube to create a fluid partial pressure about the periphery of the catheter and guide tube. Accordingly, fluid loss from the sealed catheter and guide tube prior to use is retarded and the shelf life of the apparatus thus packaged is beneficially extended.

BRIEF DESCRIPTION OF THE DRAWINGS

FIG. 1 is a view in perspective of one embodiment of the present invention with some components in section.

FIG. 2 is a partially sectional view of an apparatus for connecting a fluid filled catheter to a pressure transducer.

FIG. 3 is a view in perspective of a portion of a second embodiment of the present invention shown partially in section.

FIG. 4 is a view of the apparatus of the invention in one stage of use in its intended environment.

FIG. 5 is a view of the apparatus of the invention in another stage of use in its intended environment.

DESCRIPTION OF PREFERRED EMBODIMENTS

Figure 6:
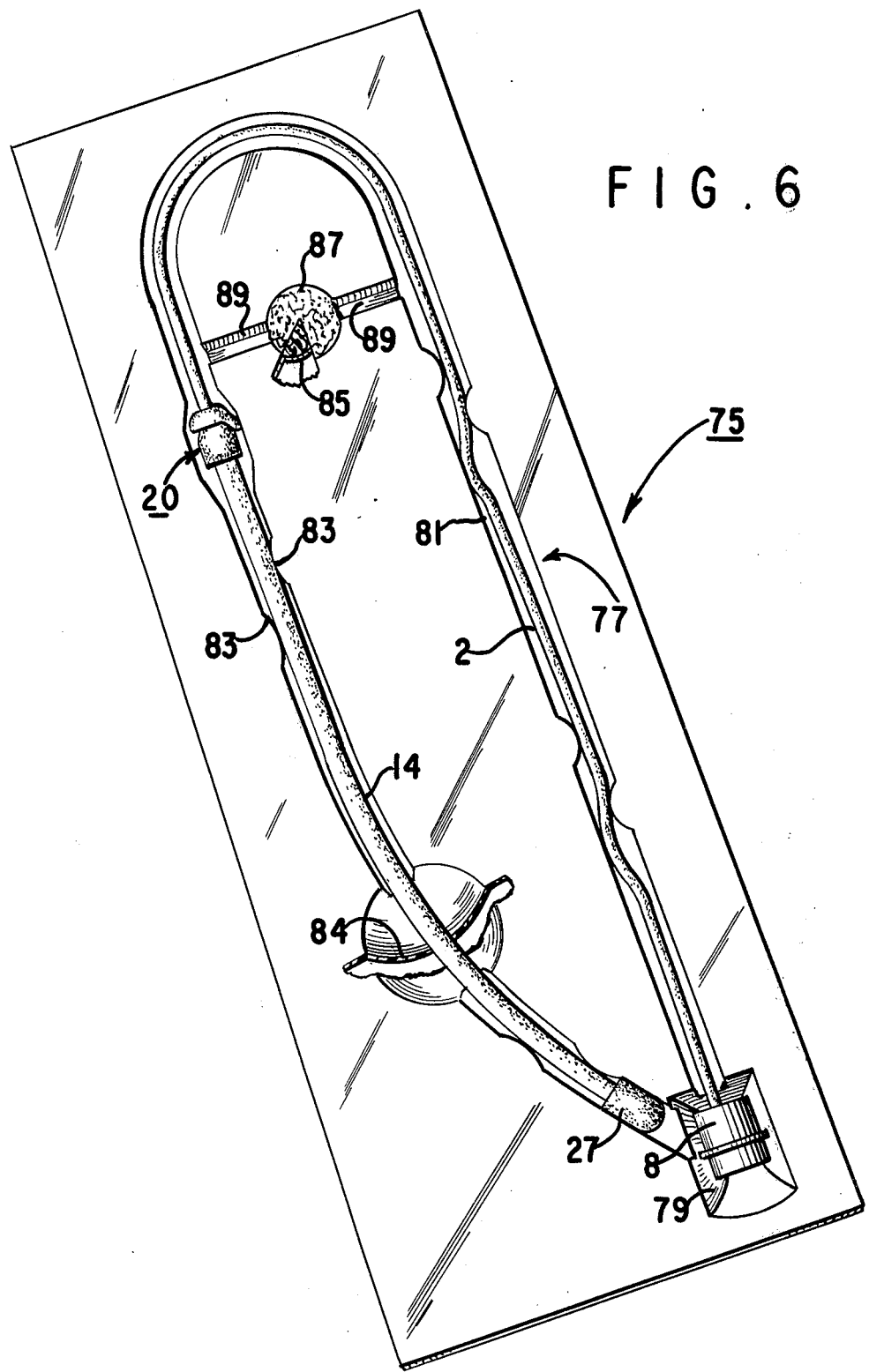
FIG. 6 is an isometric view of a preferred package for use with the present invention.

With reference to FIG. 1, there is shown a hollow elongated flexible catheter 2 having a gauge end 4 and a maternal end 6. The catheter 2 includes a multiplicity of pin holes 7 on its cylindrical surface to permit a fluid (e.g. sterile water), with which the catheter is filled, to communicate with the bodily fluids inside the uterus. For example, one hundred pin holes 7 may be formed in the catheter wall starting about two centimeters from end 6 and extending about twelve centimeters up the catheter wall. The gauge end 4 of the catheter 2 terminates in a transducer connector assembly 8 which serves to attach the gauge end of the catheter 2 to a transducer 12 (FIG. 2).

The liquid column in catheter 2 is closed at the gauge end by a pressure transmitting diaphragm 10 within transducer connector assembly 8 (FIG. 2). The diaphragm 10 can be made of a thin plastic or rubber layer or a thin material including several layers of lamination composed of one or more plastics. The thickness of the diaphragm preferably is on the order of 0.005 inches or less in order to enhance pressure transmission from the liquid within the catheter 2 to the forward surface of the transducer 12 shown in FIG. 2. Diaphragm 10 should transmit pressure fluctuations to transducer 12 with minimal energy absorption.

In assembling the apparatus of FIG. 1, the catheter 2 is disposed within a hollow elongated guide tube 14 which is formed with a curve conforming generally to the anatomical curvature of the vaginal canal of a woman. The guide tube 14 is preferably made of a material which permits it to be form-sustaining, that is, to maintain its curvature, but is pliable enough so that, during insertion through the vaginal canal, the guide tube may have its curvature temporarily altered by forces exerted upon it thereby minimizing discomfort to the patient. A suitable plastic having the aforementioned form-sustaining properties can be used.

The wall of the guide tube 14 is scored along its length as at 16 and 17 to permit the portion 15 of the guide tube wall between score lines 16 and 17 to be peeled away in a strip leaving a slot running the full length of the guide tube wall. Portion 15 is extended axially slightly beyond the gauge end of the guide tube to form a tab 18 which is grasped to peel portion 15 away from the guide tube 14. The inner diameter of the guide tube 14 is greater than the outer diameter of the catheter 2 permitting the catheter 2 to slide within the guide tube 14. The distance between the score lines 16 and 17 is large enough to permit the catheter to be passed through the slot left in the guide tube wall to separate the guide tube from the catheter. Preferably, score lines 16 and 17 are wedgeshaped in cross-section, extending through about 80% of the thickness of the wall, and formed during extrusion of the guide tube 14.

A stretchable, tubular member 20 (shown in section) having an inner diameter smaller than the outer diameter of guide tube 14 is fitted frictionally at one end 21 over the gauge end of guide tube 14. The tubular member 20 has an inner diameter larger than the outer diameter of catheter 2. The other end 22 of member 20 overlaps catheter 2 and is forced thereagainst to form a frictional seal therewith, preferably by rolling end 22 of catheter 2 axially over a portion of itself thus to force the inner surface of member 20 frictionally against catheter 2. Accordingly, guide tube 14 is releasably secured against axial movement relative to catheter 2 and a fluid tight seal with catheter 2 is formed at the guage end of guide tube 14. Member 20 can be made of any suitably stretchable material, such as silicone or latex rubber. Various other means for forcing end 22 of member 20 frictionally against catheter 2 can be used. For example, a band may be wound releasably over the outer surface of end 22 to constrict the inner surface 23 against catheter 2.

The seal and coupling of catheter 2 and guide tube 14 at its gauge end is easily released by unrolling end 22 of member 20. However, this operation is further facilitated by the provision of an axial tab 25 integral with member 20 at end 22 thereof, such that the user need only grasp and pull tab 25 to release the seal.

The body end of guide tube 14 is open to permit the catheter to be advanced therethrough easily at the time of use. A cap 27 is fitted frictionally over the body or maternal end of guide tube 14 to releasably seal it against loss of fluid therefrom prior to use. Cap 27 may be made, for example, of an elastomeric material such as silicone, natural or latex rubber.

Referring now to FIGS. 1 and 2, the transducer connector assembly 8 includes a collar 39 having an inner tapered surface for engaging catheter 2, holding it frictionally. A stainless steel cylinder (not shown) may be inserted in the gauge end of catheter 2 to maintain its outer surface in frictional contact with the inner surface of collar 39. A disc 40 extends from collar 39 in a plane transverse to the axis of the end portion 4 of the catheter. Extending axially beyond the plane of the projections 40 from the collar 39 is a cylindrical portion followed by a hollow hemispherical dish-like portion or pressure dome terminating in a stepped cylindrical ring of widened outer diameter and having an inner circular shoulder which receives a ring 41 sealing the diaphragm 10 to the shoulder. Affixed to disc 40 are two semicircular discs 42 on which there are formed integral fins extending axially which have outer surfaces 44, respectively, and in the interior of which there are inwardly sloping grasping surfaces 48, respectively.

Slidably mounted about the outer surfaces 44 of the fins for longitudinal movement along an axis extending from the catheter 2 there is a locking nut 52 having a grasping portion in the shape of an annular flange 54 on its exterior and a hollow cylindrical interior. The grasping flange 54 extends radially from the locking nut 52 to enable the nut 52 to be slid over the surfaces 44 when the transducer connector assembly 8 is attached to the transducer 12. As the nut 52 is slid over the fins, it exerts inward pressure on the surfaces 44 forcing the fins inwardly to grasp the transducer housing.

The transducer 12 is housed in a generally cylindrical enclosure having an annular flange 56 tapered outwardly to a rim 58. When the diaphragm 10 is in intimate contact with the surface of transducer 12, a portion of the inward grasping surfaces 48 of the prongs 42 is in radial alignment with the rim 58. To disengage the catheter from the transducer the nut 52 is slid toward the maternal end of the catheter 2 thereby releasing the prongs 42 so that the catheter 2 with collar 39 and nut 52 may be axially displaced from the transducer 12 until complete separation is achieved.

Transducer 12 is mounted preferably on a leg plate 34 of the type disclosed in the abovementioned U.S. Pat. No. 4,252,131, from which appropriate electrical leads connect the transducer with electronic monitoring apparatus.

With reference to FIG. 3, an alternative embodiment is shown wherein elements corresponding to those shown in FIG. 1 are indicated by the same reference numerals. The body end of catheter 2 is provided with a bulbous tip 28. A stretchable, tubular member 29 frictionally engages the body end of guide tube 14 and bulbous tip 28 to form a fluid tight seal. When in use, this seal is not broken until the guide tube is withdrawn from the body cavity. At that time tip 28 serves to restrain passage of member 29 into the body cavity upon removal of the catheter therefrom.

In the embodiment of FIG. 3, tubular member 20 is cut axially at end 21 into four fingers 30. The provision of fingers 30 facilitates removal of the tubular member 20 from guide tube 14 to permit its separation from catheter 2 and provides means for retaining tubular member 29 in the event it remains on the body end of guide tube 14 upon removal thereof from the body cavity.

FIGS. 4 and 5 illustrate a method of applying the catheter 2 to a patient using the apparatus of FIG. 1. First, the cap 27 is removed. To insert the catheter, it and the guide tube 14 are gently pushed into the vagina and through the vaginal canal until the physician feels that the maternal end of the guide tube is adjacent the cervix (FIG. 4). The tubular member 20 is unrolled to release the frictional connection between catheter 2 and guide tube 14, and the catheter 2 is pushed through and beyond the body end of the guide tube 14. Body end 6 thus penetrates the cervix and enters the uterus (FIG. 5). The guide tube 14 is then axially pulled along the catheter from the vaginal canal with one hand while the catheter is maintained in position with the other until the maternal end of the guide tube clears the vagina. Tubular member 20 is removed from the gauge end of the guide tube 14. The strip 15 between score lines 16 and 17 can then be peeled from the guide tube 14 and discarded leaving a slot in the guide tube 14.

Still holding the catheter in place with one hand the physician then pulls the catheter 2 through the slot in the guide tube 14 and continues this motion until the guide tube 14 is fully removed from about the catheter 2. The fluid-filled catheter 2 remains in proper position in the uterus. The transducer connector assembly 8 at the gauge end of the catheter 2 can be connected to the transducer 12 before or after insertion of the catheter 2 into the patient. The transducer 12 is electrically wired to a fetal monitor or other electrical device suitable to display or analyze the uterine pressure information carried by the electrical signals from the transducer.

In a method of applying a catheter to a patient using the apparatus of FIG. 3, the body end of the guide tube remains sealed by member 29 until the catheter is to be advanced past the body end of the guide tube 14, through the cervix and into the uterus. In other respects, the apparatus of FIG. 3 is applied in the same manner as that of FIG. 1. In either case, tubular member 20 can be held on collar 39 after removal from guide tube 14. When guide tube 14 is removed from the body cavity, member 29 (FIG. 3) is removed from the body end of the guide tube and wedged between the fingers 30 of member 20 and catheter 2.

In manufacturing the apparatus of FIG. 1, a catheter subassembly is provided by applying the transducer connector assembly 8 to the gauge end of the perforated guide tube 2. The guide tube 14 is then slid over the body end 6 of catheter 2 with the tubular member 20 frictionally coupled to the gauge end of the guide tube. The gauge end 22 of member 20 is rolled axially over itself to force inside surface 23 frictionally against catheter 2. The catheter-guide tube assembly is then evacuated with the unsealed body end immersed in distilled water. Then the vacuum is released, filling the catheter and guide tube with water. Cap 27 is applied over the body end of guide tube 14, so that the entire assembly is sealed.

In a modified method for manufacturing the apparatus of FIG. 3, guide tube 14 is first slid onto catheter 2 from the gauge end and is positioned over the body end of the catheter such that bulbous tip 28 projects slightly therebeyond. The body end of the guide tube 14 carries member 29 which does not yet seal the body end thereof. Tubular member 20 is folded to seal the gauge end of guide tube 14 as described hereinabove and the catheter and guide tube are then filled with distilled water through the open body end of guide tube 14 in the same manner as described for the FIG. 1 apparatus. Then guide tube 14 is slid toward the body end of catheter 2 until member 29 engages bulbous tip 28 to seal the body end of the apparatus.

With reference to FIG. 6, the sealed catheter and guide tube assembly is packaged in a low fluid vapor transmissivity enclosure having a substrate 75 with a thermally formed product space 77. Suitable materials for substrate 75 having low vapor transmissivity include polyesters. The product space 77 is shaped to conform to the catheter-guide tube assembly and includes a first well 79 for accommodating transducer connector assembly 8 and an elongated channel 81 communicating with well 79 and shaped to conform to the shape and dimensions of the catheter and guide tube. Indentations 83 in channel 81 serve to wedge catheter 2 therebetween to restrain movement of catheter 2 during shipping and handling. Product space 77 has a widened depression 84 which facilitates grasping guide tube 14 for removal therefrom.

A second well 85 in substrate 75 holds a generally cylindrical foam reservoir 87 filled with distilled water. Channels 89 connect well 85 with product space 77. A laminated sheet (not shown) formed of plastic, foil and paper is affixed to substrate 75 to seal product space 77, well 85 and connecting channels 89 thus to form a substantially closed system.

Through evaporation of water from reservoir 87, the water vapor pressure on the outer surface of the catheter-guide tube assembly is increased. Accordingly, loss of water from the catheter-guide tube assembly is retarded and the shelf life thereof is beneficially increased. After packaging, the apparatus is sterilized by irradiation, and may then be delivered for use.

Various different materials may be used to make the individual parts of the invention. Polyethylene is suitable for use as the catheter tube 2 and the guide tube 14. The transducer connector assembly 8 may be made from polycarbonate.

Although the foregoing description has related primarily to measurement of uterine pressure, the invention may be employed to measure fluid pressure in various bodily cavities.

I claim:

1. An apparatus for use in measuring the pressure within a body cavity comprising an elongated catheter filled with liquid and having a gauge end adapted to be connected to a transducer and a perforated body end adapted to be inserted into said body cavity; a guide tube adapted to define a path within the body through which said catheter is to be advanced, said guide tube having a gauge end and a body end, the body end of said catheter being positioned within said guide tube; and connector means releasably securing said catheter in a fixed relation to said guide tube, the improvement wherein:

said connector means comprises a first stretchable, tubular member having first and second ends and an inner diameter intermediate the outside diameters of said guide tube and said catheter, said intermediate diameter being further selected so that when said first end of said tubular member is placed around the gauge end of said guide tube, a frictional, fluid tight seal is formed therebetween, and the second end of said tubular member forms a loose fit around said catheter, said tubular member being further adapted to be rolled axially back on a portion of itself at said second end to force said member frictionally against said catheter to hold said catheter and said guide tube in fixed relation, and to form a fluid tight seal therebetween.

2. The apparatus of claim 1, further comprising a releasable seal preventing fluid leakage from said guide tube at the body end thereof.

3. The apparatus of claim 2, wherein said releasable seal comprises a cap adapted to fit over the body end of said guide tube.

4. The apparatus of claim 2, wherein said releasable seal comprises a second stretchable, tubular member frictionally engaging both said catheter and guide tube at their respective body ends.

5. The apparatus of claim 4, wherein said catheter further comprises a bulbous tip at the body end thereof and said second tubular member is frictionally engaged therewith to form a seal with said catheter, whereby accidental passage of said second tubular member from said catheter and into said body cavity is restrained.

6. The apparatus of claim 4 wherein the body end of said first tubular member is cut axially to provide a plurality of fingers for retaining said second tubular member against the catheter after said guide tube is removed.

7. A method of introducing the apparatus of claim 2 into a body cavity, comprising the steps of:

releasing the fluid tight seal at the body end of the guide tube;

advancing the catheter and guide tube into the body cavity;

releasing the fluid tight seal of said first tubular member by unrolling said second end of said member; and removing the guide tube from the body cavity.

8. The apparatus of claim 1, wherein said first tubular member further comprises a tab at said second end which may be grasped and pulled to unroll said first tubular member, whereby the frictional, fluid tight seal with said catheter may be released.

9. The apparatus of claim 8, wherein said tab comprises an integral section of said first tubular member.

* * * * *